United States Patent

Hanayama et al.

[11] Patent Number: 5,169,885
[45] Date of Patent: Dec. 8, 1992

[54] BIS[2-TERT-BUTYL-4-(2-OCTADECYLOX-YCARBONYLETHYL)-6-METHYLPHENYL]-PHOSPHITE USEFUL AS A STABILIZING AGENT

[75] Inventors: Naoki Hanayama, Nakatsu; Kazuo Nakagawa, Yokkaichi; Nobuyuki Hayashi, Yawata; Akiyoshi Onishi, Yokkaichi, all of Japan

[73] Assignees: Yoshitomi Pharmaceutical Industries, Ltd., Osaka; Mitsubishi Petrochemical Company, Ltd., Tokyo, both of Japan

[21] Appl. No.: 601,774

[22] PCT Filed: Mar. 1, 1990

[86] PCT No.: PCT/JP90/00273
§ 371 Date: Oct. 30, 1990
§ 102(e) Date: Oct. 30, 1990

[87] PCT Pub. No.: WO90/10008
PCT Pub. Date: Sep. 7, 1990

[30] Foreign Application Priority Data
Mar. 3, 1989 [JP] Japan .................. 1-52507
Sep. 26, 1989 [JP] Japan .................. 1-249565

[51] Int. Cl.$^5$ .............. C08K 5/526; C07F 9/145
[52] U.S. Cl. .................. 524/152; 558/198; 585/3; 554/4
[58] Field of Search .............. 558/198; 524/152

[56] References Cited

U.S. PATENT DOCUMENTS
4,094,855  6/1978  Spivack .................. 558/198

FOREIGN PATENT DOCUMENTS
2359845   2/1978  France .
59-04629  1/1984  Japan .
1580914  12/1980  United Kingdom .

Primary Examiner—Mary C. Lee
Assistant Examiner—Michael G. Ambrose
Attorney, Agent, or Firm—Wenderoth, Lind & Ponack

[57] ABSTRACT

Phosphite compounds of the formula

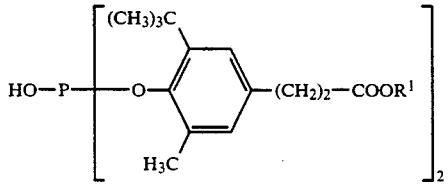

wherein $R^1$ is an alkyl having 1 to 22 carbon atoms, and use thereof.

The phosphite compounds of the present invention show stabilizing action on organic materials and are useful as antioxidants. A combined use of the compounds of the present invention with hindered phenol compounds, light stabilizers or thioalkanoate compounds further improves stabilizing effect.

7 Claims, No Drawings

BIS[2-TERT-BUTYL-4-(2-OCTADECYLOXYCARBONYLETHYL)-6-METHYLPHENYL]PHOSPHITE USEFUL AS A STABILIZING AGENT

FIELD OF THE ART

The present invention relates to phosphite compounds which are useful as stabilizing agents for organic materials and to their use.

BACKGROUND ART

Since organic materials which consist of natural macromolecule, synthetic macromolecule, fats and oils, lubricants, working oil, or so on are subject to oxidation and decrease in utility, various antioxidants have been devised and have been added to these organic materials. It is known that stabilizers such as hindered phenol compounds, thioalkanoate compounds, organic phosphorus compounds and aromatic amines have stabilizing effects when used singly or in combination. The above-mentioned stabilizing agents have their respective merits and are useful. However, there have been strong demands in recent years for the improvement in processing technology and for high quality molded products. In particular, phosphite compounds which belong to organic phosphorus compounds are widely used as useful antioxidants.

As concrete examples of phosphite compounds, there have been known the compounds which are described in the gazettes of Japanese Patent Application Examined Publication (Kokoku) No. 1641/1958 and Japanese Patent Application Unexamined Publication (Kokai) No. 4629/1984. The attempts to obtain stabilizing effects by the combined use of phosphite compounds and hindered phenol compounds have been disclosed in the gazette of Japanese Patent Application Examined Publication (Kokoku) No. 12373/1962, in the specification of U.S. Pat. No. 3,558,554, in the gazette of Japanese Patent Application Unexamined Publication (Kokai) No. 109050/1976 and in the gazette of Japanese Patent Application Examined Publication (Kokoku) No. 21822/1987. Further, there are disclosed phosphite antioxidants in U.S. Pat. Nos. 4,163,007, 4,182,704 and 4187212.

However, the above-mentioned phosphite compounds hitherto known include various problems such that sufficient stabilizing effect cannot be expected since the phosphite compounds are susceptible to hydrolysis and thermal decomposition, and inconveniences such as corrosion and foul-smelling due to the decomposed product are apt to occur. To solve these problems, there have been proposed phosphite compounds improved in resistance to hydrolysis and thermal decomposition. However, such compounds are not satisfactory but pose another problem in that advantageous properties of the hitherto-known phosphite compounds, such as protection of coloring at an initial stage during addition and kneading and that of thermal coloring in resin processing, are impaired. For example, tris[n-octadecyl-β-(3,5-di-t-butyl-4-hydroxyphenyl)propionate]phosphite [Japanese Patent Application Unexamined Publication (Kokai) No. 4629/1984], tris(2,6-ditert-butylphenyl)-phosphite, etc. pose problems mentioned above, and in addition, the bulky structure in the neighbourhood of the phosphite bond renders synthesis thereof very difficult, making themselves inadequate as an antioxidant to be supplied in a large amount.

The present inventors synthesized and evaluated tris[2-tert-butyl-6-methyl-4-(2-octadecyloxycarbonylethyl)phenyl]-phosphite in order to overcome difficulties in the synthesis of the above-mentioned tris compounds to find that heat stability was improved, whereas no improvement was observed in color tone.

Meanwhile, U.S. Pat. No. 4,182,704 discloses bis(2,6-ditert-butyl-4-ethylcarbo-n-octadecyloxyphenyl ester)-phosphite. However, the compound is not sufficient in its effect, and the bulky structure of tert-butyl in the neighbourhood of the phosphite bond renders mass production thereof unattainable.

DISCLOSURE OF THE INVENTION

Accordingly, the object of the present invention is to provide phosphite compounds showing well-balanced stabilizing effect, which are easily synthesized industrially, scarcely decomposed by heat or hydrolysis, capable of improving processing stability and heat resistance of organic materials, and further, capable of protection of initial stage coloring and thermal coloring of organic materials; and use thereof.

The present invention relates to the phosphite compound represented by the formula

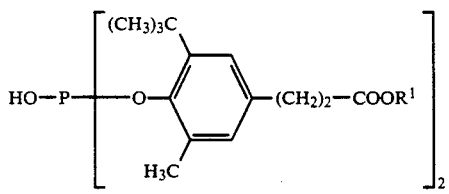

wherein $R^1$ represents an alkyl having 1 to 22 carbon atoms [hereinafter referred to as compound (I)].

In the above-mentioned definition, the alkyl having 1 to 22 carbon atoms includes, for example, methyl, ethyl, propyl, isopropyl, butyl, isobutyl, sec-butyl, tert-butyl, pentyl, isopentyl, neopentyl, tert-pentyl, hexyl, isohexyl, 1-methylpentyl, heptyl, octyl, 2-ethylhexyl, 1,1,3,3-tetramethylbutyl, nonyl, decyl, undecyl, dodecyl, tridecyl, tetradecyl, pentadecyl, hexadecyl, heptadecyl, octadecyl, nonadecyl, eicosyl, docosyl, etc.

The compounds of the formula (I) of the present invention have the following characteristics:

Firstly, it is an essentially critical difference that the commercially available phosphite compounds are tris-substituted compounds, while the compounds of the present invention are bis-substituted compounds. That is, as is clear from Example 2 mentioned below, the compounds of the present invention as a whole exhibit more excellent effects as an antioxidant in the aspects of hydrolysis, heat stability, coloring, etc. as compared with the corresponding tris-substituted compounds. Such marked difference in action due to the substituted portion is beyond prediction for those skilled in the art.

Secondly, it is important that in the formula (I), the substituent at the 4-position of the phenyl nucleus is not a simple alkyl group such as methyl group, ethyl group, propyl group, butyl group, octyl group, nonyl group or dodecyl group, but a group of the formula —(CH$_2$)$_2$—COOR$^1$. That is, the structure of the substituent at the 4-position is not restricted particularly in the synthesis of the compound (I). Besides, the substituent is an important factor to impart necessary properties as a stabilizing agent, such as solubility to organic compounds or organic materials to be stabilized, high molecular weight of the compound (I) for prevention of volatilization, and decomposition resistance.

Thirdly, it is significantly meaningful that the compounds (I) have a methyl group at the 6-position. That is, the compounds substituted by sterically bulky group such as tert-butyl group at the 6-position are extremely difficult to be synthesized, and are substantially distinguishable from the compounds (I).

Fourthly, it is vastly important from the structural viewpoint that the compounds simultaneously possess the first to the third characteristics mentioned above. For example, when a compound satisfies only the first and the third characteristics, namely, having —CH$_2$—COOR$^1$ or —COOR$^1$ at the 4-position of phenyl nucleus, the compound has an insufficient effect in color protection or heat aging resistance. Thus, it is not possible to easily predict an effective chemical structure on the basis of a combination of structures conventionally known as effective in various aspects.

As the concrete examples of the compound (I), the following can be mentioned.

Bis[2-tert-butyl-6-methyl-4-(2-(methoxycarbonyl)ethyl) phenyl]hydroxyphosphite

Bis[2-tert-butyl-6-methyl-4-(2-(butoxycarbonyl)ethyl) phenyl]hydroxyphosphite

Bis[2-tert-butyl-6-methyl-4-(2-(2-ethylhexyloxycarbonyl) ethyl)phenyl]hydroxyphosphite Bis[2-tert-butyl-6-methyl-4-(2-(dodecyloxycarbonyl)ethyl) phenyl]hydroxyphosphite Bis[2-tert-butyl-6-methyl-4-(2-(tridecyloxycarbonyl)ethyl) phenyl]hydroxyphosphite Bis[2-tert-butyl-6-methyl-4-(2-(octadecyloxycarbonyl)ethyl) phenyl]hydroxyphosphite Bis[2-tert-butyl-6-methyl-4-(2-(dococyloxycarbonyl)ethyl) phenyl]hydroxyphosphite The compounds (I) can be produced by reacting a compound of the formula

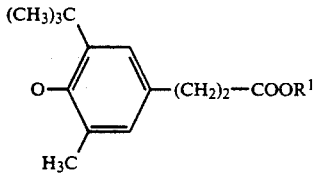

wherein R$^1$ is as defined above [hereinafter referred to as compound (II), with a compound of the formula

wherein X is a halogen atom [hereinafter referred to as compound (III)].

The reaction between the compound (II) and the compound (III) normally proceeds in a solvent such as benzene, toluene, hexane, heptane, diethyl ether, tetrahydrofuran, chloroform, carbon tetrachloride, dichloroethane, chlorotoluene or chlorobenzene in the presence of an amine such as pyridine, dimethylformamide, triethylamine, dimethylaniline, diethylaniline and 1,8-diazabicyclo[5.4.0]undecene-7 under cooling or at a temperature ranging from room temperature to the boiling point of the solvent used, for 30 minutes to 24 hours.

The objective compound (I) obtained can be purified by a conventional means such as recrystallization, chromatography and the like.

The compounds (I) of the present invention possess stabilizing action, specifically antioxidant action on organic materials, and are useful as antioxidants for preventing deterioration caused by oxidation of organic materials.

Thus, the present invention further relates to stabilized organic materials containing 0.01-5 weight % of the compounds (I), characterized by containing the compounds (I) and hindered phenol compounds, light stabilizers or thioalkanoate compounds in an amount of 0.1-15 parts by weight per part by weight of the compounds (I) contained therein.

The organic materials to be stabilized by the compounds (I) of the present invention are exemplified by macromolecular polymers, fats and oils, mineral oils themselves and those comprising them. As the macromolecular polymers, mention can be made of polyolefin polymers or copolymers thereof such as α-olefin polymers exemplified by polyethylene, polypropylene, polybutene, poly-3-methylbutylene or ethylene-vinyl acetate copolymers and ethylene-propylene copolymers; halogen-containing synthetic resins such as poly(vinyl chloride), poly(vinyl fluoride), poly(vinylidene chloride), poly(vinylidene fluoride), brominated polyethylene, chlorinated rubber, vinyl chloride-vinyl acetate copolymers, vinyl chloride-ethylene copolymers, vinyl chloride-propylene copolymers, vinyl chloride-styrene copolymers, vinyl chloride-isobutylene copolymers, vinyl chloride-vinylidene chloride copolymers, vinyl chloridestyrene-maleic acid anhydride terpolymers, vinyl chloridestyrene-acrylonitrile copolymers, vinyl chloride-butadiene copolymers, vinyl chloride-isobutylene copolymers, vinyl chloride-propylene chloride copolymers, vinyl chloridevinylidene chloride-vinyl acetate terpolymers, vinyl chloride-acrylate copolymers, vinyl chloride-maleate copolymers, vinyl chloride-methacrylate copolymers, vinyl chloride-acrylonitrile copolymers and internal plastic polyvinyl chloride; petroleum resins; comarone resins; polystyrene; poly(vinyl acetate); acrylic resins; copolymers of styrene with other monomers (maleic anhydride, butadiene, acrylonitrile and the like); acrylonitrile-butadiene-styrene copolymers; acrylate-butadiene-styrene copolymers; methacrylate-butadiene-styrene copolymers; methacrylate resins such as poly(methyl methacrylate); poly(vinyl alcohol); poly(vinyl formal); poly(vinyl butyral); straight-chain polyesters; polyphenylene oxide; polyamides; polycarbonates; polyacetals; polyurethanes; fiber-resins; unsaturated polyester resins; phenol resins; urea resins; melamine resins; epoxy resins; silicone resins; poly(ethylene terephthalate); polyphenylene sulfide; poly(butylene terephthalate); polysulfone resins; polyethersulfone; polyetheretherketone; polyarylate; polyetherimide; polyimides; maleimide; polyamide-imide; and the like. Further, there are included rubbers such as natural rubbers, isoprene rubbers, butadiene rubbers, acrylonitrile-butadiene copolymer rubbers and blend of the above-mentioned resins.

In case where the compounds (I) of the present invention are used as stabilizing agents for organic materials, they are preferably used in a proportion of 0.01-5 weight % relative to the organic materials.

In case where the compounds (I) of the present invention are used as stabilizing agents for organic materials, they are preferably used together with hindered phenol compounds, light stabilizers or thioalkanoate compounds.

As the hindered phenol compounds, there may be mentioned, but not limited to, 2,6-di-tert-butyl-4- methylphenol, 4-hydroxymethyl-2,6-di-tert-butylphenol, 2,6-di-tert-butyl-4-ethylphenol, butylhydroxyanisole, octadecyl 3-(4-hydroxy-3,5-di-tert-butylphenyl)propionate, distearyl (4-hydroxy-3-methyl-5-tert-butyl)benzylmalonate, propyl gallate, octyl gallate, dodecyl gallate, tocopherol, 2,2'-methylenebis(4-ethyl-6-tert-butylphenol), 4,4'-methylenebis(2,6-di-tert-butylphenol), 4,4'-butylidenebis(6-tert-butyl-m-cresol), 4,4'-thiobis(6-tert-butyl-m-cresol), styrenated phenol, N,N'-hexamethylenebis(3,5-di-tert-butyl-4-hydroxyhydrocinnamide), 3,5-di-tert-butylhydroxybenzylphosphonic acid aminoethyl ester calcium, 1,1,3-tris(2-methyl-4-hydroxy-5-tert-butylphenyl)butane, 1,3,5-trimethyl-2,4,6-tris(3,5-di-tert-butyl-4-hydroxybenzyl)benzene, tetrakis[3-(3,5-di-tert-butyl-4-hydroxyphenyl)propionyloxymethyl]methane, 1,6-hexanediolbis[3-(3,5-di-tert-butyl-4-hydroxyphenyl)propionate], 2,2'-dihydroxy-3,3'-dicyclohexyl-5,5'-dimethylphenylmethane, 2,2'-methylenebis[6-(1-methylcyclohexyl)-p-cresol], 1,3,5-tris(4-tert-butyl-3-hydroxy-2,6-dimethylbenzyl)isocyanuric acid, 1,3,5-tris(3,5-di-tert-butyl-4-hydroxybenzyl)-s-triazine-2,4,6(1H,3H,5H)-trione, triethyleneglycolbis[3-(3-tert-butyl-4-hydroxy-5-methylphenyl)propionate], 2,2'-oxamidebis[ethyl 3-(3,5-di-tert-butyl-4-hydroxyphenyl)propionate], 6-(4-hydroxy-3,5-di-tert-butyl-butylanilino)-2,4-dioctylthio-1,3,5-triazine, bis[2-tert-butyl-4-methyl-6-(2-hydroxy-3-tert-butyl-5-methylbenzyl)phenyl]terephthalate, 3,9-bis[2-[3-(3-tert-butyl-4-hydroxy-5-methylphenyl)propionyloxy]-1,1-dimethylethyl]-2,4,8,10-tetra-oxaspiro[5.5]undecane, 3,9-bis[2-[3-(3,5-di-tert-butyl-4-hydroxyphenyl)propionyloxy)-1,1-dimethylethyl]-2,4,8,10-tetraoxaspiro[5.5]undecane, and the like.

As the light stabilizers, there may be mentioned salicylate compounds, benzophenone compounds, benzotriazole compounds, cyanoacrylate compounds, nickel compounds or 2,2,6,6-tetramethylpiperidine compounds, such as phenyl salicylate, p-tert-butylsalicylate, p-octylphenyl salicylate, 2,4-dihydroxybenzophenon, 2-hydroxy-4-acetoxyethoxybenzophenon, 2-hydroxy-4-methoxybenzophenon, 2,2'-dihydroxy-4,4'-methoxybenzophenon, 2-hydroxy-4-n-octyloxybenzophenon, 2-hydroxy-4-isooctyloxybenzophenon, 2-hydroxy-4-dodecyloxybenzophenon, 2-hydroxy-4-octadecyloxybenzophenon, 2,2'-dihydroxy-4,4'-dimethoxy-5,5'-disulphobenzophenon 2 sodium, 2-hydroxy-4-(2-hydroxy-3-metacryloxy)propoxybenzophenon, 2-(2-hydroxy-5-methylphenyl)benzotriazole, 2-(2-hydroxy-3,5-ditert-butylphenyl)benzotriazole, 2-(2-hydroxy-3-tert-butyl-5-phenyl)benzotriazole, 2-(2-hydroxy-3-tert-butyl-5-methylphenyl)-5-chlorobenzotriazole, 2-(2-hydroxy-3,5-di-tertbutylphenyl)-5-chlorobenzotriazole, 2-(2-hydroxy-di-tertbutylphenyl)benzotriazole, 2-(2-hydroxy-3,5-di-tertbutylphenyl)benzotriazole, 2-(2-hydroxy-5-tert-octylphenyl)benzotriazole, 2,4-di-tert-butylphenyl 3,5-di-tert-butyl-4-hydroxybenzoate, ethyl 2-cyano-3,5-diphenylacrylate, [2,2-thiobis(4-tert-octylphenolate)]-n-butylamine nickel, nickel bis(octylphenylsulfide), nickel bis[O-ethyl (3,5-di-tertbutyl-4-hydroxybenzyl)]phosphonate, bis(2,2,6,6-tetramethyl-4-piperidyl)sebacate, bis(1,2,2,6,6-pentamethyl-4-piperidyl)-n-butyl-3,5-di-tert-butyl-4-hydroxybenzylmalonate, bis(1-acryloyl-2,2,6,6-tetramethyl-4-piperidyl) bis(3,5-di-tertbutyl-4-hydroxybenzyl)malonate, tetrakis(2,2,6,6-tetramethyl-4-piperidyl)butane-1,2,3,4-tetracarboxylate, poly {[6-(1,1,3,3-tetramethyl-4-piperidyl)amino]-s-triazine-2,4-diyl}, poly {[(2,2,6,6-tetramethyl-4-piperidyl)imino]hexamethylene[(2,2,6,6-tetramethyl-4-piperidyl)imino]}, poly(6-morpholino-s-triazine-2,4-di-yl)[(2,2,6,6-tetramethyl-4-piperidyl)imino]hexamethylene[(2,2,6,6-tetramethyl-4-piperidyl)imino], 1-hydroxyethyl-2,2,6,6-tetramethyl-4-piperidinol/succinic acid condensate, cyanuric chloride/tertoctylamine/1,6-bis(2,2,6,6-tetramethyl-4-piperidylamino)hexane condensate, with preference given to benzotriazole compounds and 2,2,6,6-tetramethylpiperidine compounds.

The thioalkanoate compound is selected from a group consisting of dilauryl thiodipropionate, dimyristyl thiopropionate, distearyl thiodipropionate and pentaerythritol tetrakis($\beta$-laurylthiopropionate).

When the compounds (I) of the present invention are used as stabilizing agents for organic materials together with at least one species selected from among hindered phenol compounds, light stabilizers and thioalkanoate compounds, it is preferable that the amount thereof be 0.01–5 weight % relative to the organic materials, and the hindered phenol compounds, etc. are preferably used in an amount of 0.1–15% by weight relative to the compounds (I) of the present invention.

The methods of blending the compounds (I) solely, or in combination with hindered phenol compounds, light stabilizers or thioalkanoate compounds, into organic materials include mixing, kneading, extrusion, etc.

The compounds (I) of the present invention can be used further in combination with metal soaps, heavy metal inactivation agents, nucleator, organic tin compounds, plasticizers, epoxy compounds, pigments, fillers, foaming agents, anti-electrifying agents, flame-retardants, lubricants, process auxiliaries, and the like.

The compounds (I) of the present invention exhibit stabilizing action on organic materials and are useful as an antioxidant. The combined use thereof with hindered phenol compounds, light stabilizers or thioalkanoate compounds induces further-improved stabilizing effect.

Hereafter, the present invention is shown by examples which is not to be construed as limitative. The compounds obtained below were confirmed to be the objective compounds (I) by means of infrared absorption spectrum, nuclear magnetic resonance spectrum, mass spectrum, elemental analysis, etc.

EXAMPLE 1

In a 1 l-flask were charged methyl 3-(3-tert-butyl-5-methyl-4-hydroxyphenyl)propionate (98.2 g) and toluene (400 ml), and pyridine (1.9 g) was added dropwise thereto. The temperature thereof was raised, and phosphorous trichloride (16.3 g) was added dropwise at 70° C. After addition, the temperature of the mixture was raised and the mixture was stirred under reflux at 110°–112° C. for 13 hours. After completion, the reaction mixture was poured into water and extracted with ethyl acetate, followed by washing with water. The mixture was dehydrated with anhydrous magnesium sulfate, and the solvent was distilled off to give crude product (120.1 g). The precipitated crystals were filtered off, and the filtrate was purified by silica gel column chromatography (solvent: n-hexane: ethyl acetate=5:1), after which it was combined with the precipitated crystals, and recrystallized from a mixed solvent of n-hexane and ethyl acetate (7:1) to give bis[2-tert-butyl-6-methyl-4-(2-(methoxycarbonyl)ethyl)phenyl]-hydroxyphosphite (50.6 g) as white crystalline powder, m.p. 138°–139° C.

The FAB mass spectrum of this product showed hydrogenated molecular ion at m/z=547.

| Elemental analysis (%) | | | |
|---|---|---|---|
| Measured | C: 65.70, | H: 8.10, | P: 5.70 |
| Calculated | C: 65.92, | H: 7.93, | P: 5.67 |

EXAMPLE 2

Octadecyl 3-(3-tert-butyl-5-methyl-4-hydroxyphenyl)propionate (70.0 g) and pyridine (3.5 ml) were added to toluene (80 ml), and the mixture was heated to 70° C., to which was added dropwise phosphorous trichloride (7.14 g) over 15 minutes. After addition, the mixture was stirred under reflux with toluene for 10 hours. The reaction mixture was cooled, added with water (150 ml), and extracted twice with ethyl acetate. The organic layer was washed with water (150 ml) and saturated brine (200 ml), after which it was dried with anhydrous magnesium sulfate, and the solvent was distilled off. The obtained crude product (63.4 g) was purified by silica gel column chromatography (solvent: a mixed solvent of n-hexane and ethyl acetate), and recrystallized from a mixed solvent of n-hexane and methanol (1:1) to give bis[2-tert-butyl-6-methyl-4-(2-(octadecyloxycarbonyl)ethyl)-phenyl]hydroxyphosphite (15.9 g), m.p. 68.5°–70° C.

The FAB mass spectrum of this product showed hydrogenated molecular ion at m/z=1023.

| Elemental analysis (%) | | | |
|---|---|---|---|
| Measured | C: 75.00, | H: 10.90, | P: 3.00 |
| Calculated | C: 75.10, | H: 10.93, | P: 3.03 |

Octadecyl 3-(3-tert-butyl-5-methyl-4-hydroxyphenyl) propionate, a starting material, was synthesized as follows.

Methyl 3-(3-tert-butyl-5-methyl-4-hydroxyphenyl)-propionate (70.0 g), octadecyl alcohol (76.3 g) and dibutyltin oxide (0.74 g) were dissolved in toluene (70 ml), after which the mixture was heated, and the solvent (200 ml) was distilled off while adding toluene. The toluene was distilled off from the reaction mixture and the residue was purified by column chromatography to give octadecyl 3-(3-tert-butyl-5-methyl-4-hydroxyphenyl)propionate (136.0 g), m.p. 58°–59° C.

PRODUCTION EXAMPLE 1

Methyl 3-(3-tert-butyl-5-methyl-4-hydroxyphenyl)-propionate (10.0 g), toluene (40 ml) and 1,8-diazabicyclo[5.4.0]undecene-7(DBU) (6.1 g) were mixed and phosphorous trichloride (1.7 g) was dropwise added thereto at 25° C. After addition, the mixture was stirred at 25°–26° C. for 17 hours. After the reaction, the mixture was poured into water and extracted with ethyl acetate. The mixture was washed with water, dried over anhydrous magnesium sulfate, and concentrated under reduced pressure, after which it was purified by silica gel column chromatography [solvent: a mixed solvent of n-hexane and ethyl acetate (5:1)]. The obtained crude product was recrystallized from n-hexane to give tris[2-tertbutyl-6-methyl-4-(2-(methoxycarbonyl)ethyl)phenyl]phosphite as white crystalline powder, m.p. 113°–114° C.

The FAB mass spectrum of this product showed hydrogenated molecular ion at m/z=779.

| Elemental analysis (%) | | | |
|---|---|---|---|
| Measured | C: 69.30, | H: 8.10, | P: 3.80 |
| Calculated | C: 69.39, | H: 8.15, | P: 3.98 |

PRODUCTION EXAMPLE 2

In a 200 ml-flask were charged octadecyl 3-(3-tert-butyl-5-methyl-4-hydroxyphenyl)propionate (20.0 g), toluene (60 ml) and DBU (6.2 g), and phosphorous trichloride (1.4 g) was added dropwise thereto at 23°–29° C. Following addition, the mixture was stirred at 25°–28° C. for 19 hours. After the reaction, the mixture was poured into water, extracted with ethyl acetate and washed with water. After dehydration over anhydrous magnesium sulfate, the solvent was distilled off. The obtained crude product was purified by silica gel column chromatography [solvent: n-hexane and ethyl acetate (10:1)], and recrystallized from n-hexane to give tris[2-tert-butyl-6-methyl-4-(2-(octadecyloxycarbonyl)ethyl)phenyl]phosphite as white crystalline powder, m.p. 65°–66° C.

The FAB mass spectrum of this product showed hydrogenated molecular ion at m/z=1493.

| Elemental analysis (%) | | | |
|---|---|---|---|
| Measured | C: 76.90, | H: 11.00, | P: 2.10 |
| Calculated | C: 77.16, | H: 11.13, | P: 2.07 |

EXPERIMENT EXAMPLE 1

An antioxidant was added to polypropylene powder having an intrinsic viscosity of 1.9 when measured in tetralin at 135° C., 98% of which is isotactic ones with no additive, and the mixture was well mixed in a mixer. The mixture was melted and kneaded with an extruder of a diameter of 20 mm with a ratio of L/D=20 at a cylinder temperature of 260° C. to granulates. The MFR (JIS K6758) at 230° C. of the thusobtained pellets was measured and taken as $MFR_1$. Further, the mixture was subjected to extrusion 3 times repeatedly under the above-mentioned kneading and granulation conditions. The MFR at 230° C. of the thus-obtained pellets was taken as $MFR_4$. MFR is one of the indexes for molecular weight. The higher the MFR is, the smaller the molecular weight is. That is, if $MFR_1$ and $MFR_4$ are lower and the balance of $MFR_1$ and $MFR_4$ is small, it means that the decrease in molecular weight owing to oxidation and deterioration in the extruder is small, and further, if the antioxidants have been used, that the antioxidant effects thereof are high. The results are summarized in Table 1. As a control compound, tris(2,4-ditert-butylphenyl)phosphite (hereinafter referred to as compound A), which is a representative compound among the compounds disclosed in U.S. Pat. No. 4,187,212 was employed.

TABLE 1

| | antioxidant | $MFR_1$ | $MFR_4$ |
|---|---|---|---|
| present | compound of Ex. 1 | 0.05 PHR | 6.5 | 13.7 |
| invention | compound of Ex. 2 | 0.05 PHR | 6.7 | 14.1 |
| comparison | compound A | 0.05 PHR | 7.5 | 71.6 |
| example | none | | 12.8 | 92.3 |

EXPERIMENT EXAMPLE 2

Procedures of Experiment Example 1 were followed except that tetrakis[3-(3,5-di-tert-butyl-4-hydroxyphenyl)propionyloxymethyl]methane (hereinafter referred to as compound B) was used as a hindered phenol compound, and the antioxidant effect was examined. The results are summarized in Table 2. In Table, hue b shows b value of Hunter and YI shows a yellowness index. The 1st and the 4th extruded pellets are shown in a comparative manner. The smaller the value is, the smaller the coloring degree is. As the control compounds, compound A, tris[2-tert-butyl-6-methyl-4-(2-(methoxycarbonyl) ethyl)phenyl]phosphite (compound of Production Example 1) and tris[2-tert-butyl-6-methyl-4-(2-(octadecyloxycarbonyl)ethyl) phenyl]phosphite (compound of Production Example 2) were used.

TABLE 2

| antioxidant | MFR$_4$/MFR$_1$ | hue b value | YI |
|---|---|---|---|
| present invention | | | |
| compound of Ex. 1 | 0.1 PHR | 4.07/ | 2.74/ 6.74/ |
| compound B | 0.1 PHR | 1.42 | 1.03 1.99 |
| compound of Ex. 2 | 0.1 PHR | 4.43/ | 2.24/ 5.21/ |
| compound B | 0.1 PHR | 1.77 | 0.81 1.35 |
| comparison example | | | |
| compound A | 0.1 PHR | 4.30/ | 4.62/ 11.87/ |
| compound B | 0.1 PHR | 1.53 | 2.15 4.97 |
| comp. of Prod. Ex. 1 | 0.1 PHR | 13.23/ | 4.35/ 11.21/ |
| compound B | 0.1 PHR | 3.25 | 2.09 4.77 |
| comp. of Prod. Ex. 2 | 0.1 PHR | 15.36/ | 4.67/ 12.05/ |
| compound B | 0.1 PHR | 3.04 | 2.24 5.10 |

EXPERIMENT EXAMPLE 3

To the polypropylene resin used in Experiment Example 1 was added a phosphorous antioxidant shown in Table 3, and they were thoroughly mixed. The mixture was pelletized at 260° C. using a 20 mm φ extruder. Thereafter, 1 mm thick test pieces were prepared by an injection molding machine.

The obtained test piece was placed in a gear oven adjusted to 150°±1° C., and the time up to the brittle point was measured (BP, hours). The results are shown in Table 3.

TABLE 3

| phosphorous antioxidant | amount added (%) | BP (hours) |
|---|---|---|
| compound of Ex. 2 | 0.05 | 60 |
| compound A | 0.05 | 10 |
| compound of Prod. Ex. 2 | 0.05 | 10 |
| blank | — | 5 |

EXPERIMENT EXAMPLE 4

To the polypropylene resin employed in Experiment Example 1 were added a phosphorous antioxidant mentioned in Table 4 and calcium stearate, and they were thoroughly mixed. The same procedure as in Experiment Example 3 was followed and the time up to the brittle point was measured. The results are shown in Table 4.

TABLE 4

| phosphorous antioxidant | amount added (%) | BP (hours) |
|---|---|---|
| compound of Ex. 2 | 0.1 | 180 |
| calcium stearate | 0.1 | |
| compound A | 0.1 | 10 |

TABLE 4-continued

| phosphorous antioxidant | amount added (%) | BP (hours) |
|---|---|---|
| calcium stearate | 0.1 | |

EXPERIMENT EXAMPLE 5

To the polypropylene resin employed in Experiment Example 1 were added an antioxidant mentioned in Table 5 and tetrakis[3-(3,5-di-tert-butyl-hydroxyphenyl)propionyloxymethyl]methane (compound B), and they were thoroughly mixed. The same procedure as in Experiment Example 3 was followed and the time up to the brittle point was measured. The results are shown in Table 5.

TABLE 5

| antioxidant | amount added (%) | BP (hours) |
|---|---|---|
| compound of Ex. 2 | 0.05 | 540 |
| compound B | 0.05 | |
| compound A | 0.05 | 380 |
| compound B | 0.05 | |
| compound of Prod. Ex. 2 | 0.05 | 390 |
| compound B | 0.05 | |
| compound B | 0.05 | 280 |

EXPERIMENT EXAMPLE 6

The hydrolysis resistance of various organic phosphite compounds containing the compounds of the present invention was compared by way of measurement of weight change with time at 40° C. and in 75% relative humidity. The results are shown in Table 6.

TABLE 6

| | phosphite comp. | weight change with time (hrs) | | | |
|---|---|---|---|---|---|
| | | 0 | 60 | 120 | 180 |
| present invention | compound of Ex. 1 | 100 | 100 | 100 | 100 |
| | compound of Ex. 2 | 100 | 100 | 100 | 100 |
| comparison example | compound A | 100 | 99.9 | 99.9 | 99.9 |
| | compound C | 100 | 105.6 | 102.9 | 101.4 |
| | compound D | 100 | 108.9 | 108.7 | 108.9 |
| | compound E | 100 | 96.2 | 90.3 | 87.6 |
| | comp. of Prod. Ex. 1 | 100 | 100 | 99.9 | 99.9 |

[The initial value of various organic phosphite compounds at 0 hour was taken as 100, and the change in weight was compared. Compounds C, D and E in the Table are the following compounds respectively.
Compound C: trisnonylphenyl phosphite
Compound D: cyclicneopentanetetraylbis(octadecyl phosphite)
Compound E: cyclicneopentanetetraylbis(2,4-di-tert-butylphenyl phosphite)]

As shown in Experiment Examples 1 to 6 above, the compounds of the present invention are extremely well-balanced antioxidants.

It has been said as regards phosphite antioxidants that they prevent coloring of polymers, become phosphates themselves by oxidation, and decompose hydroperoxides which contribute to autoxidation of polymers, into inactivated compounds. In addition thereto, it has been said that as an advantageous merit, they prevent coloring caused by conversion of primary phenol antioxidants into quinone structures by oxidation, while as a demerit, they are subject to hydrolysis. Examples of such phosphite antioxidants include trisnonylphenyl phosphite (compound C), cyclicneopentanetetraylbis-(octadecylphosphite) (compound D) and cyclicneopentanetetraylbis(2,4-di-tert-butyl-phenylphosphite) (compound E). These compounds are capable of color protection and improve stability in processing, whereas as shown in Experiment Example 6, they are easily hydrolyzed.

As an example of representative phosphite compounds with improved hydrolytic stability, there may be mentioned tris(2,4-di-tert-butylphenyl)phosphite (compound A).

As is evident from the results of Experiment Example 6, the compounds of the present invention and the compounds of Production Examples which are tris compounds thereof, are useful compounds having the same or more excellent hydrolysis resistance as compared with tris(2,4-di-tert-butylphenyl) phosphite. Thus, the present inventors made a comparison as regards stabilizing capacity in processing and color protection capacity of these phosphite compounds with improved hydrolytic stability by way of Experiment Examples 1 and 2. That is, Experiment Example 1 is directed to comparison of capacity using phosphite compounds alone, and Experiment Example 2 is directed to comparison of capacity using phosphite compounds and phenol compounds together, the results of which show that as in Experiment Example 1, compound A does not show processing stability when used solely, but the compounds of the present invention have sufficient stabilizing action in sole use. As regards compound A, a method for improving processing stability has been developed, in which compound A is used alongside with phenol antioxidants in order to compensate for the insufficient effect when used alone, which has been disclosed in U.S. Pat. No. 4,187,212. Nevertheless, compound A has an insufficient effect on color protection, and also the compounds of Production Examples 1 and 2 do not show effective results on color protection, as shown in Experiment Example 2.

To the contrary, notwithstanding the fact that the compounds of the present invention have the structure quite similar to that of the compounds of Production Examples 1 and 2, they surprisingly possess hydrolysis resistance as well as color protection capacity.

Also, the present inventors made comparison of heat resistance of the phosphite compounds as shown in Experiment Examples 3 to 5. In Experiment Example 3, it has been shown that the compounds of the present invention markedly improve heat resistance of polymers as compared with other compounds even in sole use, and in Experiment Examples 4 and 5, it has been found that such heat resistance can be further improved by the co-use of other compounds.

As stated above, some of the hitherto-known phosphite compounds have as advantageous properties, color protection capacity and processing stability but are subject to easy hydrolysis, and others show hydrolysis resistance and when used with phenol antioxidants, processing stability but are inferior in color protection. Making a sharp contrast, the compounds of the present invention are balanced compounds which are capable of improving color protection, processing stability, hydrolysis resistance and heat resistance of polymers. In addition, when used together with other additives, the compounds of the present invention further improve such advantageous properties.

The present invention has been fully explained in the description and examples given above, but any variations and modifications thereof may be made without departing from the spirit and scope of the present invention.

We claim:
1. A phosphite compound of the formula

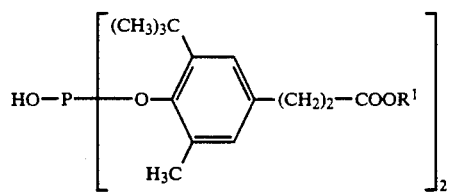

wherein $R^1$ is octadecyl.

2. A stabilized organic material selected from the group consisting of fats and oils, mineral oils, polyolefin polymers or copolymers thereof, halogencontaining synthetic resins, petroleum resins, cumarone resins, polystyrenes, poly(vinyl acetate), acrylic resins, copolymers of styrene with maleic anhydride, copolymers of styrene with butadiene, copolymers of styrene with acrylonitrile, acrylonitrile-butadiene-styrene copolymers, acrylate-butadiene-styrene copolymers, methacrylatebutadiene-styrene copolymers, poly(methyl methacrylate) resins, poly(vinyl alcohol), poly(vinyl formal), poly(vinyl butyral), straight-chain polyesters, polyphenylene-oxide, polyamides, polycarbonates, polyacetals, polyurethanes, fiber-resins, unsaturated polyester resins, phenol resins, urea resins, melamine resins, epoxy resins, silicone resins, polyethylene terephthalate, polyphenylenesulfide, polybutylene terephthalate, polysulfone resins, polyethersulfone, polyetheretherketone, polyarylate, polyetherimide, polyimides, maleimide, polyamideimide, natural rubbers, isoprene rubbers, butadiene rubbers, acrylonitrile-butadiene copolymer rubbers and blend thereof which contains 0.01-5 weight % of the phosphite compound

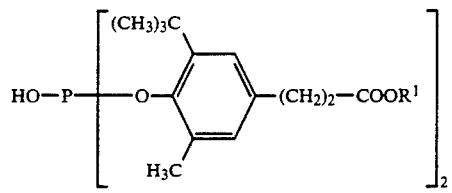

wherein $R^1$ is octadecyl.

3. The stabilized organic material of claim 2 which additionally contains a hindered phenol compound in an amount of 0.1-15 parts by weight per part by weight of said phosphite compound.

4. The stabilized organic material of claim 2 which additionally contains a light stabilizer in an amount of 0.1-15 parts by weight per part by weight of said phosphite compound.

5. The stabilized organic material as claimed in claim 4, wherein said light stabilizer is a benzotriazole UV absorber.

6. The organic material as claimed in claim 4, wherein said light stabilizer is a 2,2,6,6-tetramethylpiperidine compound.

7. The stabilized organic material of claim 2 which additionally contains thioalkanoate compound selected from the group consisting of dilauryl thiodipropionate, dimyristyl thiodipropionate, distearyl thiodipropionate and pentaerythritol tetrakis($\beta$-laurylthiopropionate) in an amount of 0.1-15 parts by weight per part by weight of said phosphite compound.

* * * * *